(12) United States Patent
Lee et al.

(10) Patent No.: US 12,268,660 B2
(45) Date of Patent: Apr. 8, 2025

(54) ORAL PHARMACEUTICAL FORMULATIONS OF BITTER COMPOUNDS FOR PULMONARY HYPERTENSION

(71) Applicant: Aardvark Therapeutics Inc., San Diego, CA (US)

(72) Inventors: Tien-Li Lee, San Diego, CA (US); Zhenhuan Zheng, San Diego, CA (US)

(73) Assignee: Aardvark Therapeutics Inc., San Diego, CA (US)

(*) Notice: Subject to any disclaimer, the term of this patent is extended or adjusted under 35 U.S.C. 154(b) by 754 days.

(21) Appl. No.: 17/257,458

(22) PCT Filed: Jul. 11, 2019

(86) PCT No.: PCT/US2019/041421
§ 371 (c)(1),
(2) Date: Dec. 31, 2020

(87) PCT Pub. No.: WO2020/014494
PCT Pub. Date: Jan. 16, 2020

(65) Prior Publication Data
US 2021/0260013 A1    Aug. 26, 2021

Related U.S. Application Data

(60) Provisional application No. 62/696,528, filed on Jul. 11, 2018.

(51) Int. Cl.
*A61K 31/216* (2006.01)
*A61K 31/167* (2006.01)
(Continued)

(52) U.S. Cl.
CPC .......... *A61K 31/216* (2013.01); *A61K 31/167* (2013.01); *A61K 45/06* (2013.01); *A61P 9/12* (2018.01)

(58) Field of Classification Search
CPC .... A61K 31/216; A61K 31/167; A61K 45/06; A61P 9/12
See application file for complete search history.

(56) References Cited

U.S. PATENT DOCUMENTS 7,939,671 B2   5/2011   Li
8,445,692 B2   5/2013   Karanewsky
(Continued)

FOREIGN PATENT DOCUMENTS

WO   WO2005030187   4/2005
WO   WO2014027981   2/2014
(Continued)

OTHER PUBLICATIONS

Zhai et al. "Activation of bitter taste receptors (tas2rs) relaxes detrusor smooth muscle and suppresses overactive bladder symptoms" Oncotarget :21156-21167, 2016.
(Continued)

*Primary Examiner* — Savitha M Rao
*Assistant Examiner* — Andrew P Lee
(74) *Attorney, Agent, or Firm* — McNeill PLLC

(57) ABSTRACT

There is disclosed an oral pharmaceutical formulation of bitter compounds that are agonists of TAS2R receptors for the treatment of pulmonary hypertension (PAH). More specifically, there is disclosed a PAH oral formulation comprising a bitter agent selected from the group consisting of 3-caffeoylquinic-1,5-lactone (3-CQL), chlorogenic acid (CGA), denatonium benzoate (DB), denatonium chloride (DC), denatonium saccharide (DS), denatonium acetate (DA), and combinations thereof and a PDE-5 inhibitor.

9 Claims, 10 Drawing Sheets

(51) Int. Cl.
 *A61K 45/06* (2006.01)
 *A61P 9/12* (2006.01)

(56) References Cited

U.S. PATENT DOCUMENTS

| | | | |
|---|---|---|---|
| 8,796,233 | B2 | 8/2014 | Goddard |
| 9,272,051 | B2 | 3/2016 | Goddard |
| 9,579,315 | B2 | 2/2017 | Liggett et al. |
| 10,330,678 | B2 | 6/2019 | Goddard |
| 10,610,500 | B2 | 4/2020 | Baron et al. |
| 10,835,505 | B2 | 11/2020 | Lee |
| 2003/0229140 | A1* | 12/2003 | Bandyopadhyay .. A61K 31/366 514/533 |
| 2004/0043057 | A1 | 3/2004 | Suzuki et al. |
| 2007/0104792 | A1 | 5/2007 | Jenkins |
| 2013/0131108 | A1 | 5/2013 | Ligget et al. |
| 2014/0030332 | A1 | 1/2014 | Baron |
| 2014/0302528 | A1 | 10/2014 | Li |
| 2018/0161298 | A1 | 6/2018 | Deretic |

FOREIGN PATENT DOCUMENTS

| | | |
|---|---|---|
| WO | WO2016/172479 | 10/2016 |
| WO | 2020/014494 A1 | 1/2020 |

OTHER PUBLICATIONS

Deckmann et al., "Bitter triggers acetylcholine release from polymodal urethral chemosensory cells and bladder reflexes" Proc. Natl. Acad. Sci. 111:8287-8292, 2014.
Upadhyaya et al., "" PLOS One 9:e110373, Dextromethorphan Mediated Bitter Taste Receptor Activation in the Pulmonary Circuit Causes Vasoconstriction.
Manson et al., "Bitter taste receptor agonists mediate relaxation of human and rodent vascular smooth muscle" Eur. J. Pharmacology 740:302-311, 2014.
Pulkkinen et al., "The bitter taste receptor (TAS2R) agonists denatonium and chloroquine display distinct patterns of relaxation of the guinea pig trachea" Am. J. Physiol. Lung Cell Mol. Physiol. 303:956-966, 2012.
Sai et al. "Bitter tastants induce relaxation of rat thoracic aorta precontracted with high K+" Clin. Exper. Pharmacology and Phys. 41:301-301, 2014.
Gassin-Delyle et al., "The expression and relaxant effect of bitter taste receptors on human bronchi" Respiratory Research 14:134, 2013.
Deloose et al. "Intragastric infusion of denatonium benzoate attenuates interdigestive gastric motility and hunger scores in healthy female volunteers1" Am. J. Clin. Nutr. 105:583-588, 2017.
Avau et al. "Targeting extra-oral bitter taste receptors modulates gastrointestinal motility with effects on satiation" Scientific Reports 5:15985 2015.
Avau et al.2 "The Gustatory Signaling Pathway and Bitter Taste Receptors Affect the Development of Obesity and Adipocyte Metabolismi n Mice" PLOS One 10.1371 2015.
Glendinning et al., "Intragastric infusion of denatonium conditions flavor aversions and delays gastric emptying in rodents" Physiol. Behav. 93:757-765, 2008.
Hao et al., "Role of CCK1 and Y2 receptors in activation of hindbrain neurons induced by intragastric administration of bitter taste receptor ligands" Am. J. Physiol. Regul. Integr. Comp. Physiol. 294:R33-R38, 2008.
Janssen et al., "Bitter taste receptors and β-gustducin regulate the secretion of ghrelin with functional effects on food intake and gastric emptying" PNAS 108:2094-2099, 2011.
Kim et al., "Denatonium induces secretion of glucagon-like peptide-1 through activation of bitter taste receptor pathways" Diabetologia 57:2117-2125, 2014.
Miyata et al. "Effect of five taste ligands on the release of CCK from an enteroendocrine cell line, STC-1" Biomedical Research 35:171-176, 2014.
Schier et al. "Ongoing ingestive behavior is rapidly suppressed by a preabsorptive, intestinal "bitter taste" cue" Am. J. Physiol. Regul. Integr. Comp. Physiol. 301:R1557-R1568, 2011.
Straub et al., "Stimulation of Insulin Secretion by Denatonium, One of the Most Bitter-Tasting Substances Known" Diabetes 52:356-364, 2003.
Meyerhof et al., "The Molecular Receptive Ranges of Human TAS2R Bitter Taste Receptors" Chem. Senses 35:157-170. 2010.
PCT/US2019/041421 written opinion.
International Search Report and Written Opinion of the International Searching Authority, mailed Oct. 7, 2019 (8 pages).

* cited by examiner

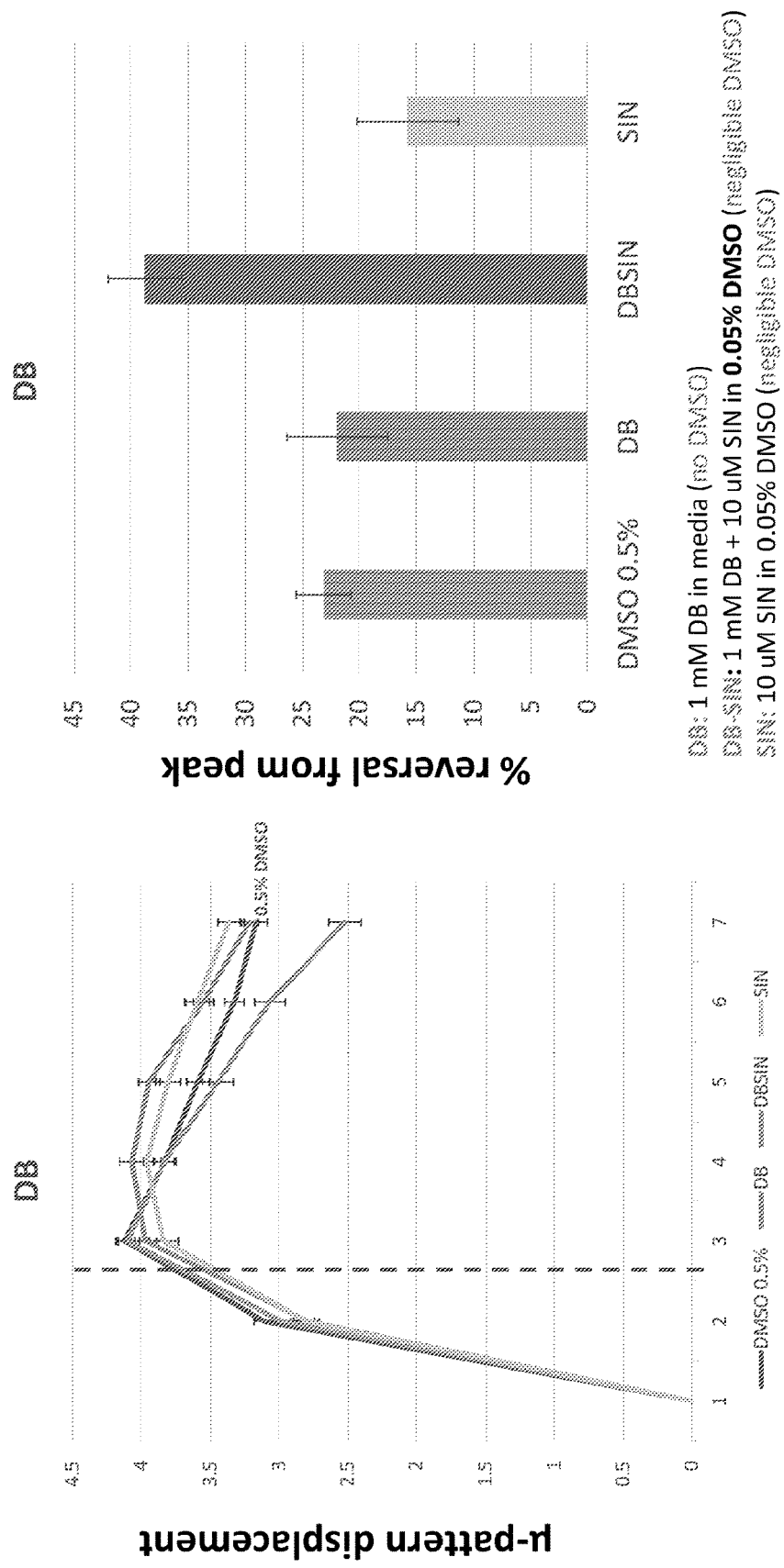

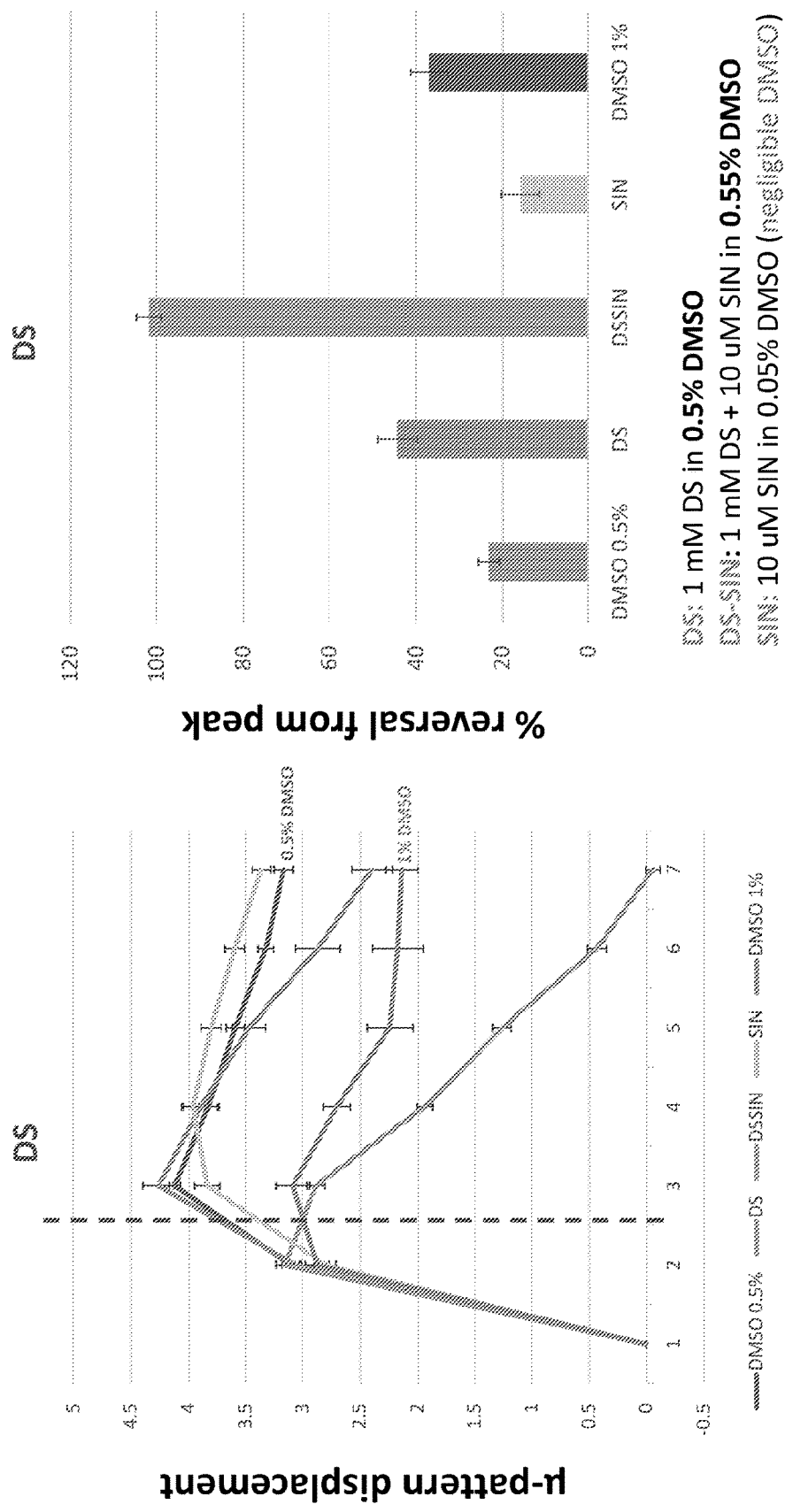
Figure 4: DS alone and in combination with SIN

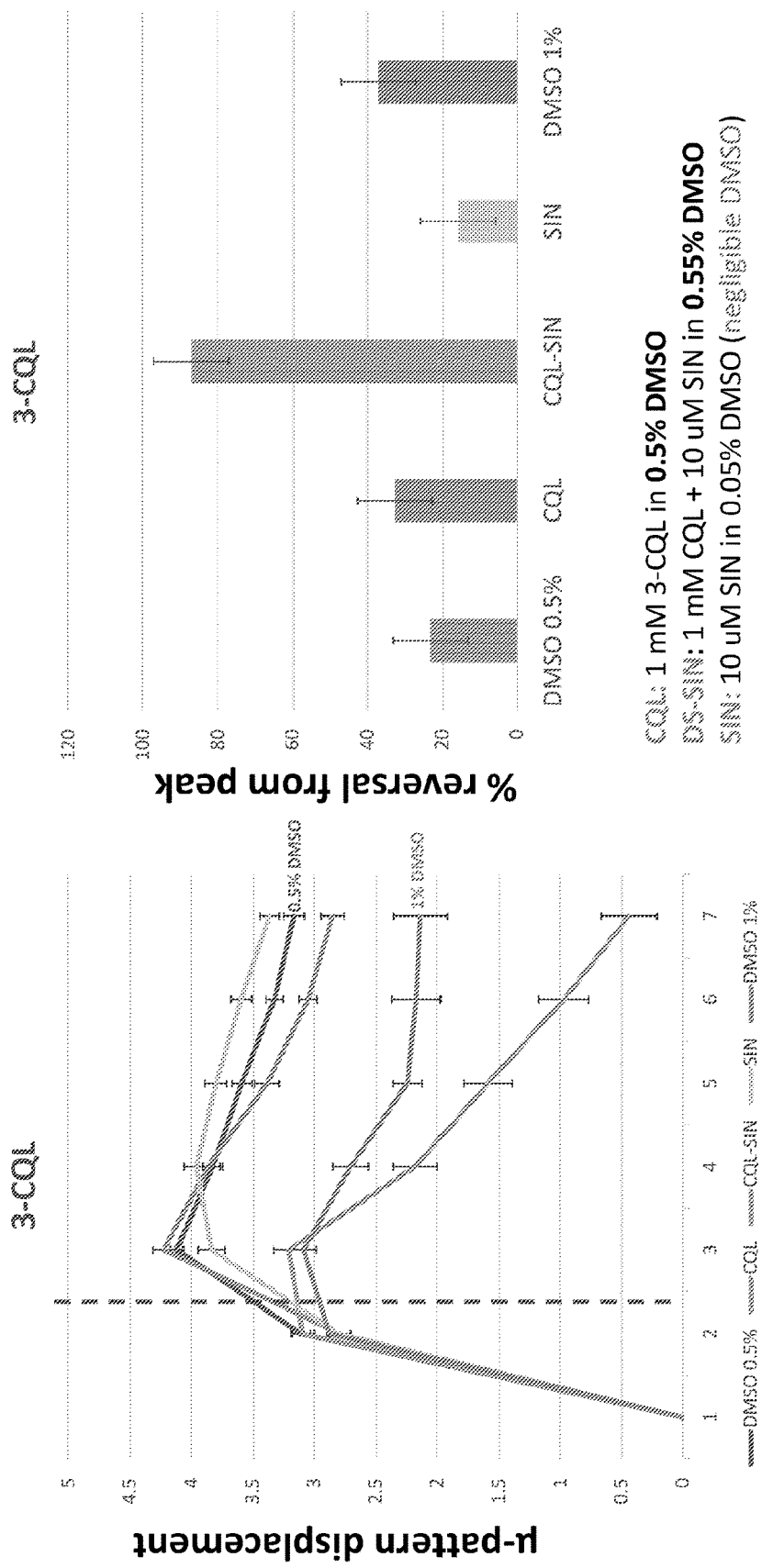
Figure 5: 3-CQL alone and in combination with SIN

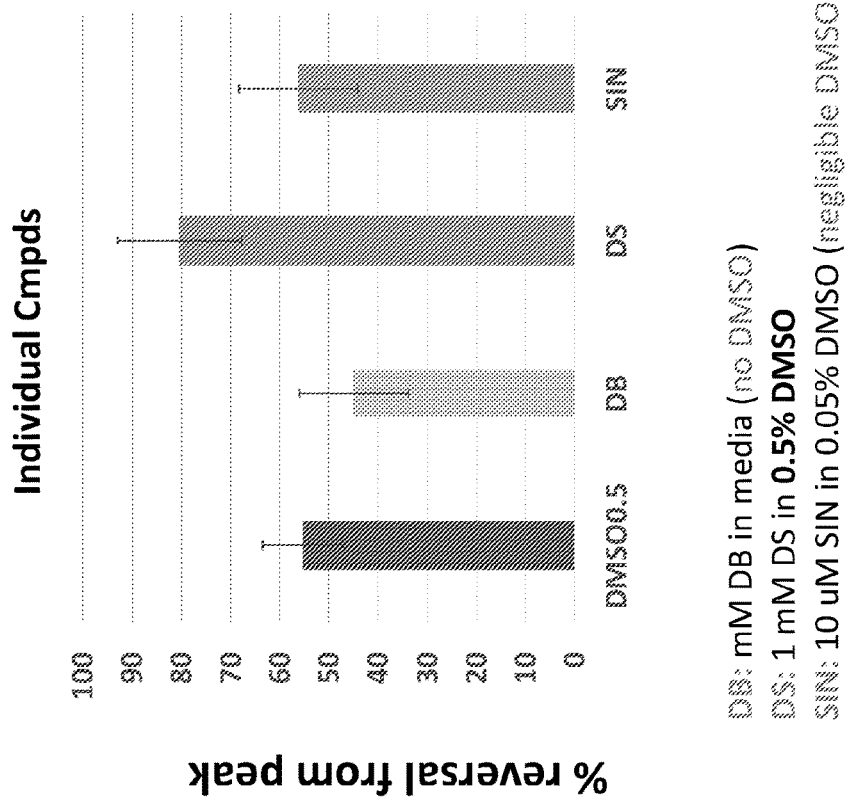
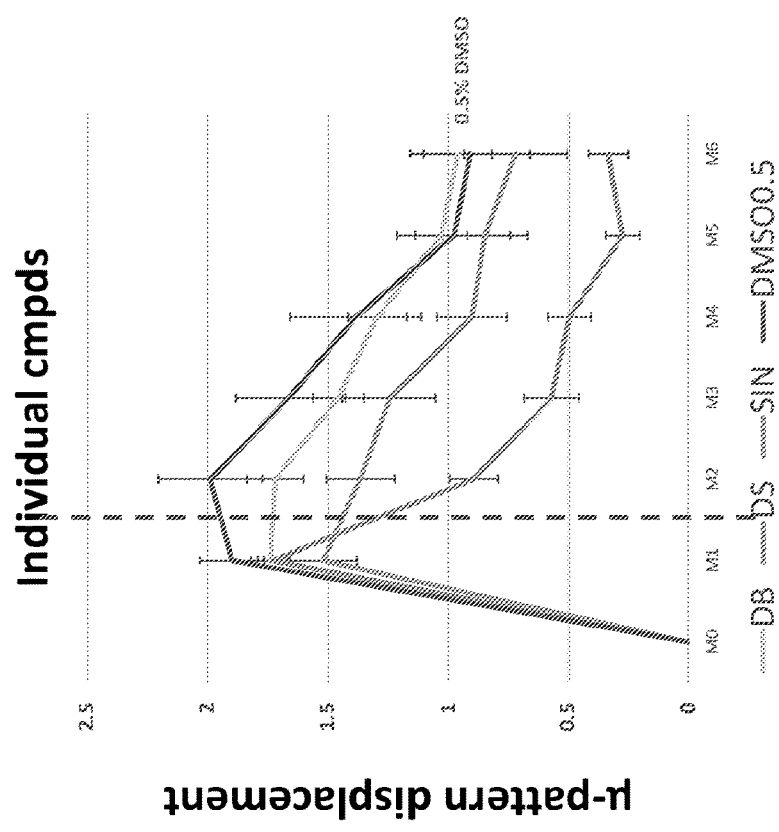
Figure 6: Phenylepherine: Individually tested AV cmpds

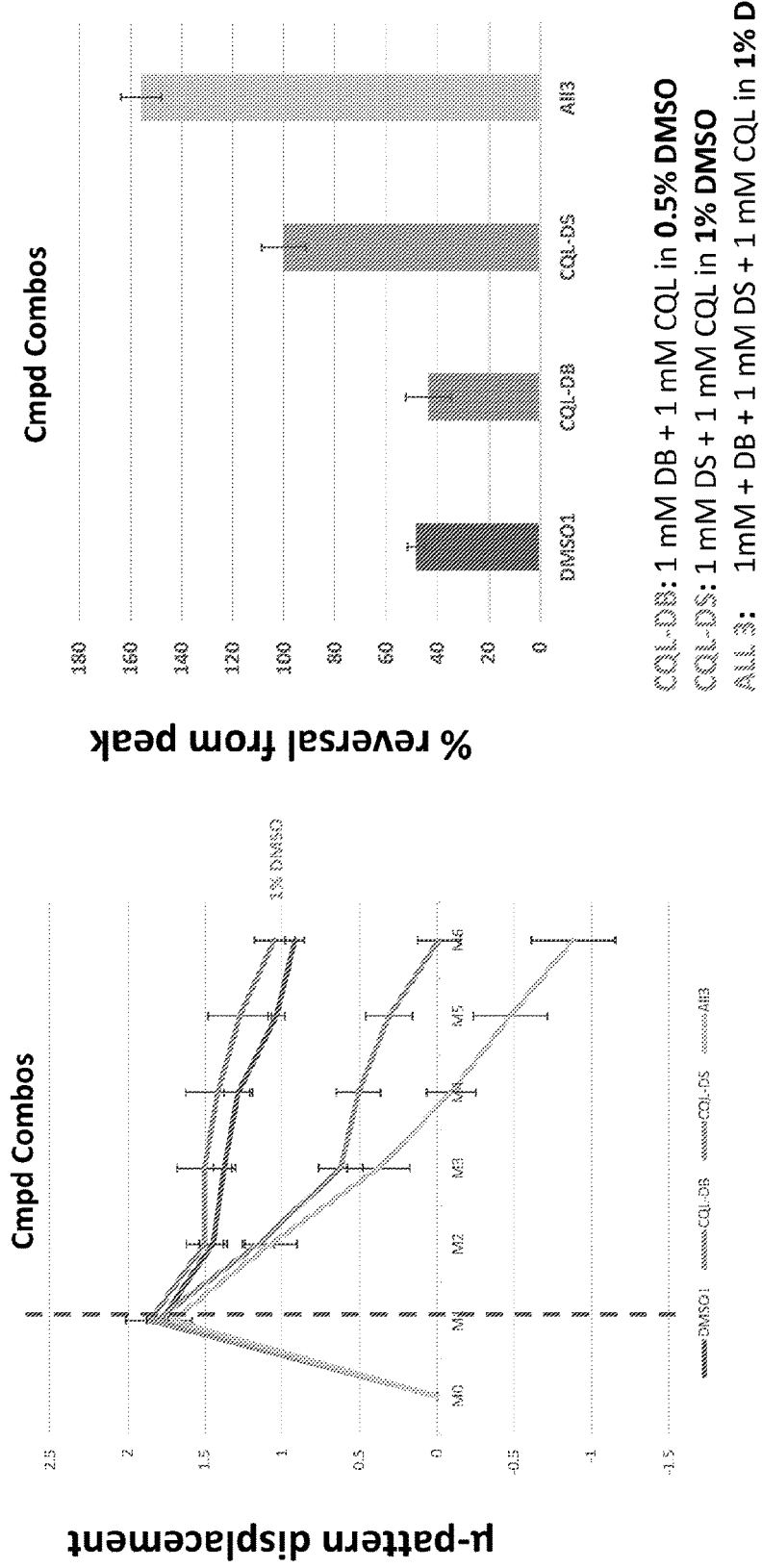
Figure 7: Phenylepherine: Combinations of AV cmpds

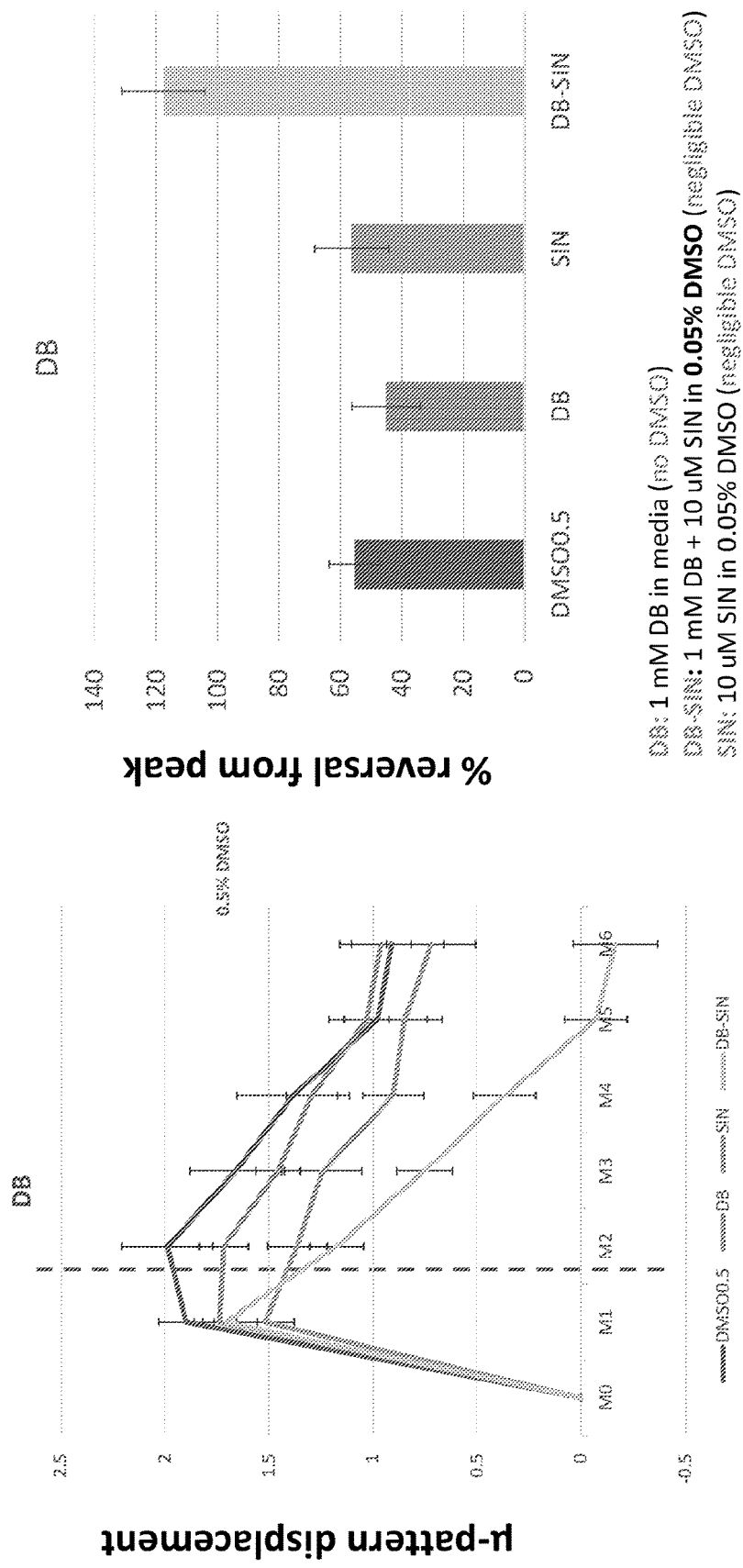
Figure 8: Phenylepherine: DB alone and in combination with SIN

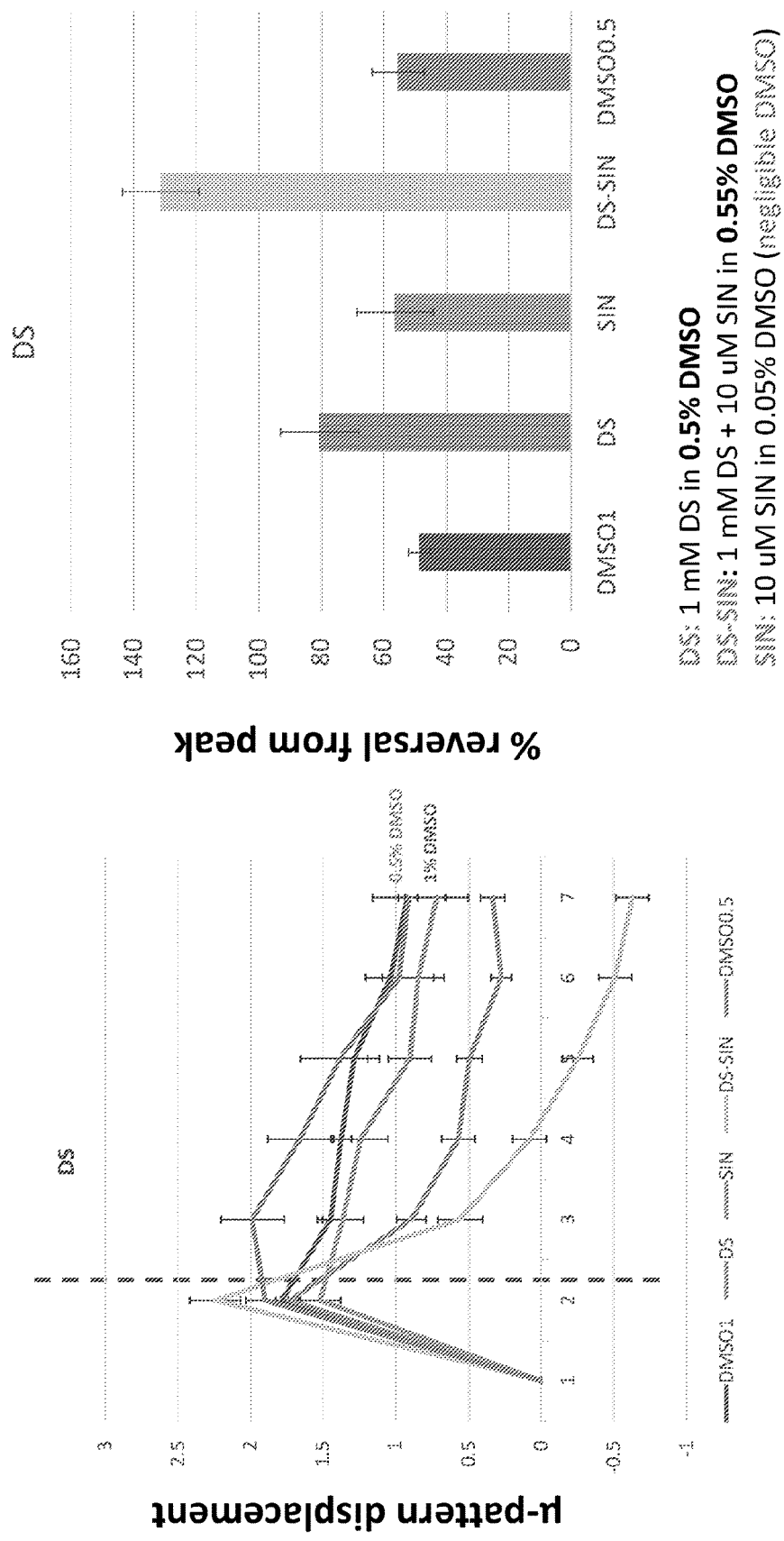
Figure 9: Phenylepherine: DS alone and in combination with SIN

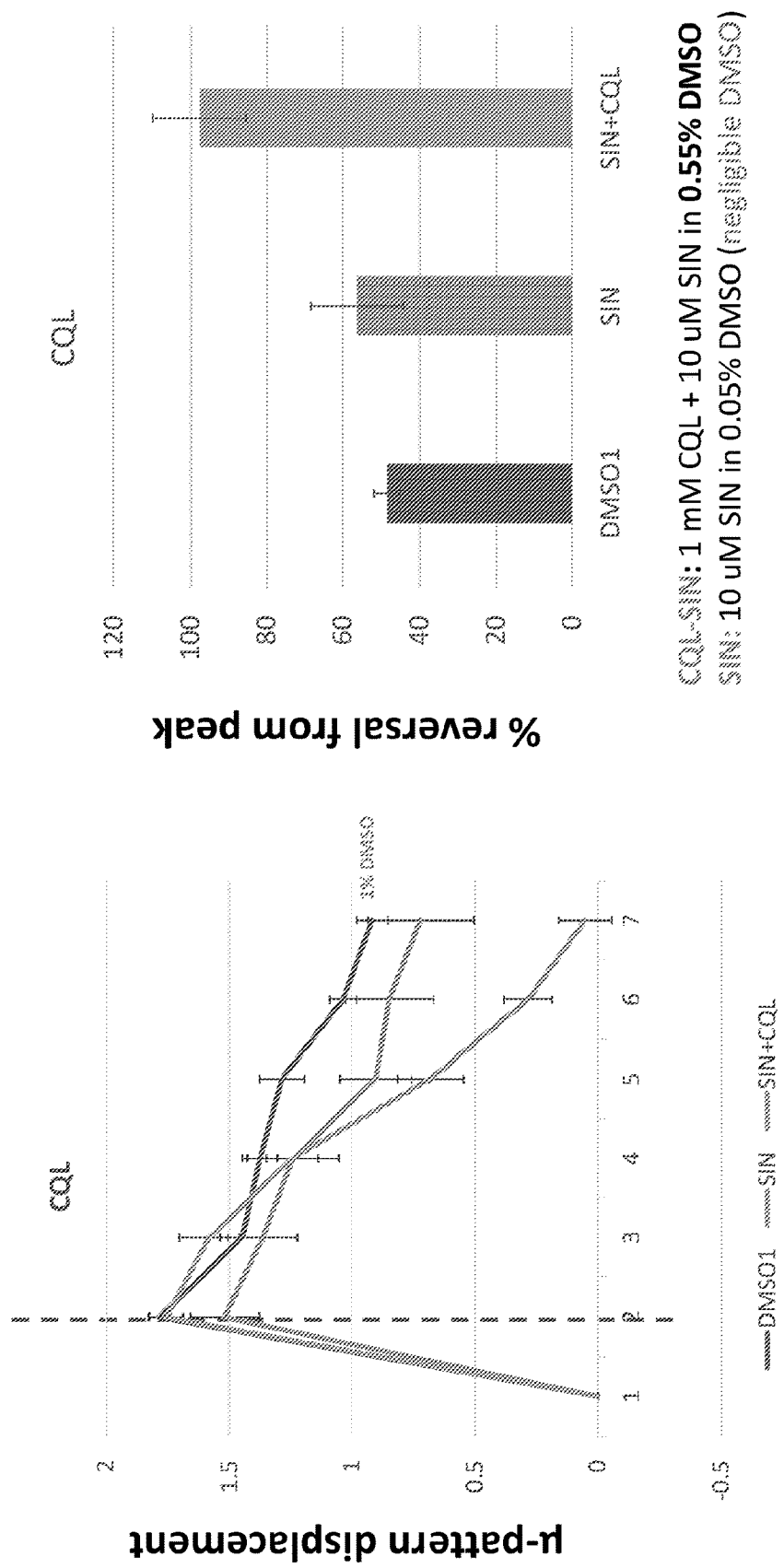
Figure 10 Phenylepherine: 3-CQL alone and in combination with SIN

ORAL PHARMACEUTICAL FORMULATIONS OF BITTER COMPOUNDS FOR PULMONARY HYPERTENSION

TECHNICAL FIELD

The present disclosure provides an oral pharmaceutical formulation of bitter compounds that are agonists of TAS2R receptors for the treatment of pulmonary hypertension (PAH). More specifically, the present disclosure provides a PAH oral formulation comprising a bitter agent selected from the group consisting of 3-caffeoylquinic-1,5-lactone (3-CQL), chlorogenic acid (CGA), denatonium benzoate (DB), denatonium chloride (DCl), denatonium citrate (DC), denatonium saccharide (DS), denatonium acetate (DA), and combinations thereof and a PDE-5 inhibitor.

BACKGROUND

Pulmonary Arterial Hypertension (PAH) is a condition in which the pressure in the lung circulation increases, eventually causing heart failure and death. Although many causes and conditions are found to be associated with PAH, many of them share in common several fundamental pathophysiological features. One feature among these processes is dysfunction of the endothelium, the internal cellular layer of all vessel walls, which is responsible for the production and metabolism of a large array of substances that regulate vessel tone and repair and inhibit clot formation. In the setting of PAH, endothelial dysfunction can lead to excessive production of deleterious substances and impaired production of protective substances. Whether this is the primary event in the development of PAH or part of a downstream cascade remains unknown, but in either case it is a factor in the progressive vasoconstriction and vascular proliferation that characterize the disease.

PAH is defined by a mean pulmonary artery pressure (PAP)>25 mm Hg at rest or >30 mg Hg with exercise. Muscularization of small (less than 500 μm diameter) pulmonary arterioles is widely accepted as a common pathological denominator of PAH, however it may also occur in other forms of PAH such as based on COPD or thrombotic and/or thromboembolic disease. Other pathoanatomical features in PAH are thickening of the intima based on migration and proliferation of (myo)fibroblasts or smooth muscle cells and excessive generation of extracellular matrix, endothelial injury and/or proliferation and perivascular inflammatory cell infiltrates. Together, remodeling of distal pulmonary arterial vasculature results in augmented pulmonary vascular resistance, consecutive right heart failure and death.

Other therapeutic approaches have been molecular aberrations in particular enhanced endothelin-1 formation, reduced prostacyclin (PG12) generation and impaired eNOS activity in PAH vasculature. Endothelin-1 acting via $ET_A$-receptors is mito-genic for pulmonary arterial smooth muscle cells and triggers acute vasoconstriction. The oral $ET_A/ET_B$-antagonist Bosentan has recently been approved in the EU and United States for treatment of PAH after the compound demonstrated improvements in clinical endpoints such as mean PAP, PVR or 6 min walking test. However, Bosentan augmented liver enzymes and regular liver tests are mandatory. Also, selective $ET_A$ antagonists such as sitaxsentan or ambrisentan are under investigation.

As another strategy in management of PAH replacement of deficient prostacyclin by $PGI_2$ analogues, such as epoprostenol, treprostinil, oral beraprost or iloprost. Prostacyclin serves as a brake to excessive mitogenesis of vascular smooth muscle cells acting to augment cAMP generation. Intravenous prostacyclin (epoprostenol) significantly improved survival rates in idiopathic pulmonary hypertension as well as exercise capacity and was approved in North America and some European countries in the mid-1990s. However, owing to its short half-life, epoprostenol has to be administered via continuous intravenous infusion, which is uncomfortable, complicate and expensive. In addition, adverse events due to systemic effects of prostacyclin are frequent. Alternative prostacyclin analogues are treprostinil, recently approved in the United States for PAH treatment and delivered via continuous subcutaneous infusion and beraprost, an orally active $PGI_2$ analogue, which has been approved for treatment of PAH in Japan. Its therapeutic profile appeared more favorable in patients with idiopathic PAH compared to other forms of pulmonary hypertension and side effects linked to systemic vasodilation following beraprost administration and local pain at the infusion site under treprostinil treatment are frequent. Administration of the prostacyclin analogue iloprost, via an inhalation route, was approved in Europe. Its beneficial effects on exercise capacity and hemodynamic parameters are to be balanced to a high dosing frequency of 6-12 courses of inhalation per day from appropriate devices. An oral therapy is needed.

Functional consequences of impaired endothelial nitric oxide formation, as reported in pulmonary arterial hypertension, may be overcome by selective inhibitors of phosphodiesterase-5 (PDE5) that is expressed in pulmonary artery smooth muscle cells. Consequently, the selective PDE5 inhibitor sildenafil was demonstrated to improve pulmonary hemodynamics and exercise capacity in PAH.

Most of these treatments primarily address smooth muscle cells function, however, in addition pulmonary vascular fibroblasts, endothelial cells but also perivascular macrophages and T-lymphocytes are considered to contribute to the development of pulmonary hypertension.

In spite of the different therapeutic approaches mentioned above the medical need to alleviate the disease burden in pulmonary hypertension is high. Thus, a need exists to develop a non-invasive therapeutic method to treat PAH.

SUMMARY

The present disclosure provides an oral pharmaceutical formulation of bitter compounds that are agonists of TAS2R receptors for the treatment of pulmonary hypertension (PAH). More specifically, the present disclosure provides a PAH oral formulation comprising a bitter agent selected from the group consisting of denatonium benzoate (DB), denatonium citrate (DC), denatonium chloride (DCl), denatonium saccharide (DS), denatonium acetate (DA), 3-caffeoylquinic-1,5-lactone (3-CQL), chlorogenic acid (CGA), and combinations thereof. Preferably the oral formulation further comprises a PDE-5 inhibitor in view of synergy shown for this combination, allowing for a lower dose of a PDE-5 inhibitor to be used. Preferably, the PDE-5 inhibitor is selected from the group consisting of sildenafil, tadafil, vardenafil, zaprinast, udenafil, microdenafil, lodenafil, and avanafil. Most preferably, the PDE-5 inhibitor is sildenafil as an oral daily dose of from about 10 mg to about 100 mg administered once or twice daily.

The present disclosure provides a PAH treatment oral formulation comprising a bitter agent selected from the group consisting of denatonium benzoate (DB), denatonium chloride (DCl), denatonium saccharide (DS), denatonium acetate (DA), denatonium citrate (DC), denatonium maleate (DM), 3-caffeoylquinic-1,5-lactone (3-CQL), chlorogenic acid (CGA), and combinations thereof. Preferably the oral formulation further comprises a PDE-5 inhibitor. Preferably, the PDE-5 inhibitor is selected from the group consisting of sildenafil, tadafil, vardenafil, zaprinast, udenafil, microdenafil, lodenafil, and avanafil. Most preferably, the PDE-5 inhibitor is sildenafil as an oral daily dose of from about 20 mg to about 100 mg administered once or twice daily. Preferably, the bitter agent for an asthma formulation is DB or DA. Preferably the daily dosage of DB or DA for an adult is from about 10 mg to about 400 mg. More preferably, the daily dosage of DB or DA for an adult is from about 10 mg to about 200 mg. Most preferably, the daily dosage of DB or DA for an adult is from about 10 mg to about 100 mg. Preferably, the bitter agent for the PAH formulation is selected from the group consisting of DA. DC, DS, 3-CQL or CGA. Preferably the daily dosage of 3-CQL or CGA for an adult is from about 10 mg to about 5000 mg. More preferably, the daily dosage of 3-CQL or CGA for an adult is from about 50 mg to about 2000 mg. Most preferably, the daily dosage of 3-CQL or CGA for an adult is from about 100 mg to about 1000 mg.

The present disclosure provides a method for treating PAH with an orally administered therapeutic formulation comprising a bitter agent selected from the group consisting of denatonium benzoate (DB), denatonium chloride (DCl), denatonium saccharide (DS), denatonium acetate (DA), denatonium citrate (DC), denatonium maleate (DM), 3-caffeoylquinic-1,5-lactone (3-CQL), chlorogenic acid (CGA), and combinations thereof. Preferably the oral formulation further comprises a PDE-5 inhibitor. Preferably, the PDE-5 inhibitor is selected from the group consisting of sildenafil, tadafil, vardenafil, zaprinast, udenafil, microdenafil, lodenafil, and avanafil. Most preferably, the PDE-5 inhibitor is sildenafil as an oral daily dose of from about 10 mg to about 100 mg administered once or twice daily. It should be noted that the synergy of the combination with a PDE-5 inhibitor (exemplified by the sildenafil data presented below) allowed for a significantly lower PAH dose of a PDE-5 inhibitor than is otherwise administered and approved for a PDE-5 inhibitor to treat PAH.

Preferably, the bitter agent for an asthma formulation is DB or DA. Preferably the daily dosage of DB or DA for an adult is from about 10 mg to about 400 mg. More preferably, the daily dosage of DB or DA for an adult is from about 10 mg to about 200 mg. Most preferably, the daily dosage of DB or DA for an adult is from about 10 mg to about 100 mg. Preferably, the bitter agent for the PAH formulation is selected from the group consisting of DA. DC, DS, 3-CQL or CGA. Preferably the daily dosage of 3-CQL or CGA for an adult is from about 10 mg to about 400 mg. More preferably, the daily dosage of 3-CQL or CGA for an adult is from about 50 mg to about 2000 mg. Most preferably, the daily dosage of 3-CQL or CGA for an adult is from about 100 mg to about 1000 mg.

BRIEF DESCRIPTION OF THE FIGURES

FIG. 3 shows results with DB alone and in combination with SIN and FIG. 4 shows results with DS alone and in combination with SIN.

FIG. 5 shows results with 3-CQL alone and in combination with SIN.

FIG. 6 shows in vitro efficacy results from individually tested compounds.

FIG. 7 shows in vitro efficacy results from combinations of compounds.

FIG. 8 shows in vitro efficacy with DB alone and in combination with SIN.

FIG. 9 shows in vitro efficacy results with DS alone and in combination with SIN.

FIG. 10 shows in vitro efficacy results with 3-CQL alone and in combination with SIN.

DETAILED DESCRIPTION

The present disclosure was discovered by the surprising results (detailed below) that not all bitter agents that are agonists of the same TAS2R receptors are effective when tested using primary human vascular endothelial cells is an in vitro model measuring stimulated smooth muscle contractile ability. Moreover, the data showed surprising synergistic ability to relax stimulated pulmonary vascular smooth muscle cells (PVSMC) when using a TAS2R receptor agonist together with lower concentrations of a different mechanism of action PDE-5 inhibitor. These data show unpredictability of TAS2R receptor agonists as treatments for PAH and synergy of a combination with a PDE-5 inhibitor, allowing for uses of lower oral doses of a PDE-5 inhibitor when administered as an oral formulation (preferably capsule) to avoid having a TAS2R agonist come into contact with bitter taste receptors in the mouth/tongue.

An in vitro model using human primary smooth muscle cells (PVSMC) were stimulated to contract with 100 nM endothelin-1, then treated with various test compounds alone and in combination with the PDE-5 inhibitor sildenafil, approved to treat PAH. The concentration used were 3-CQL at 1 mM, DB at 1 mM, DS at 1 mM and SIN (sildenafil) at 10 µM. The controls were 0.5% and 1% DMSO in media because DB is water-soluble but DS, 3-CQL and SIN are DMSO soluble.

Figure 1:
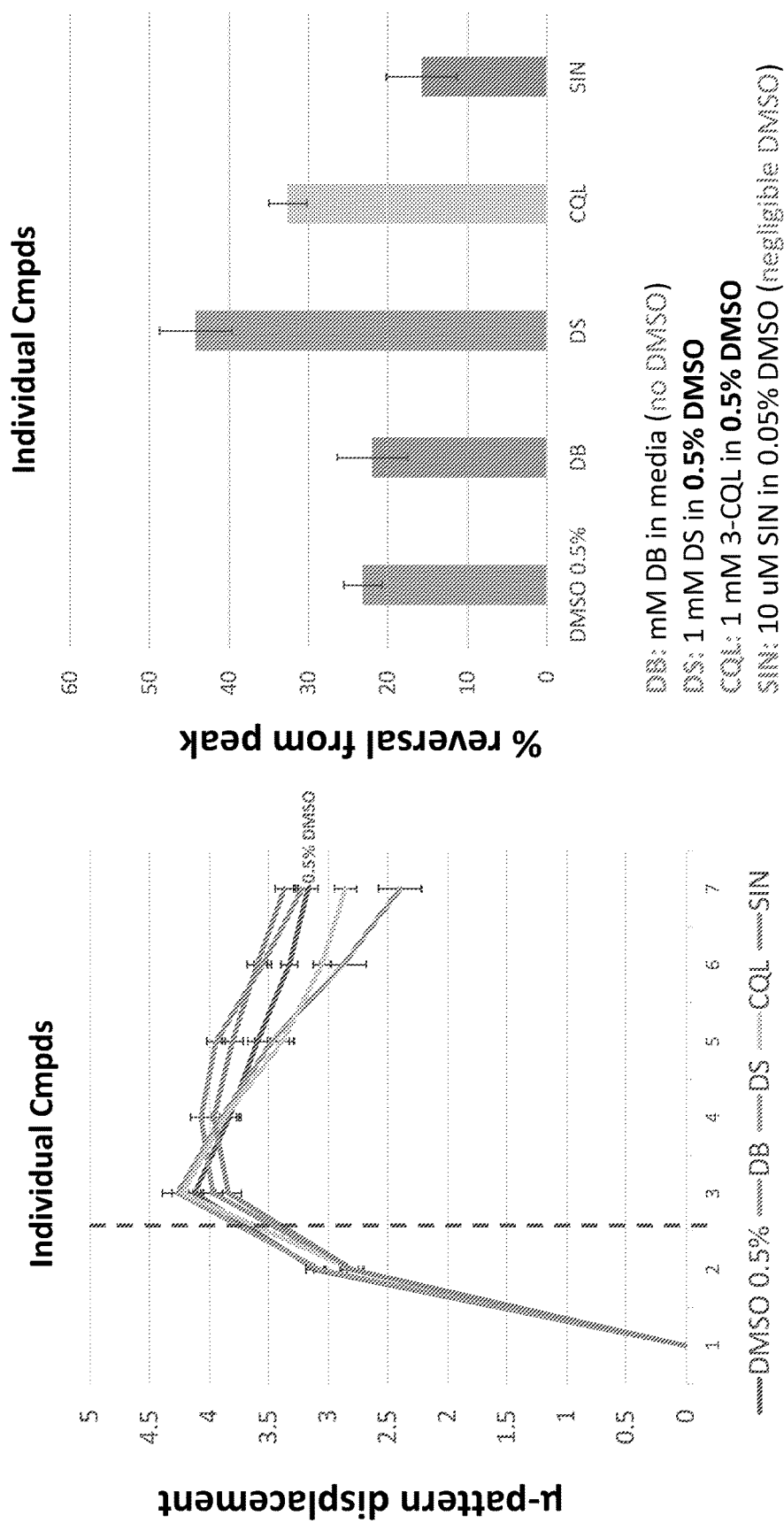
FIG. 1 shows the results of individually tested compounds as a percentage reversal from peak contraction of the PVSMCs.
Figure 2:
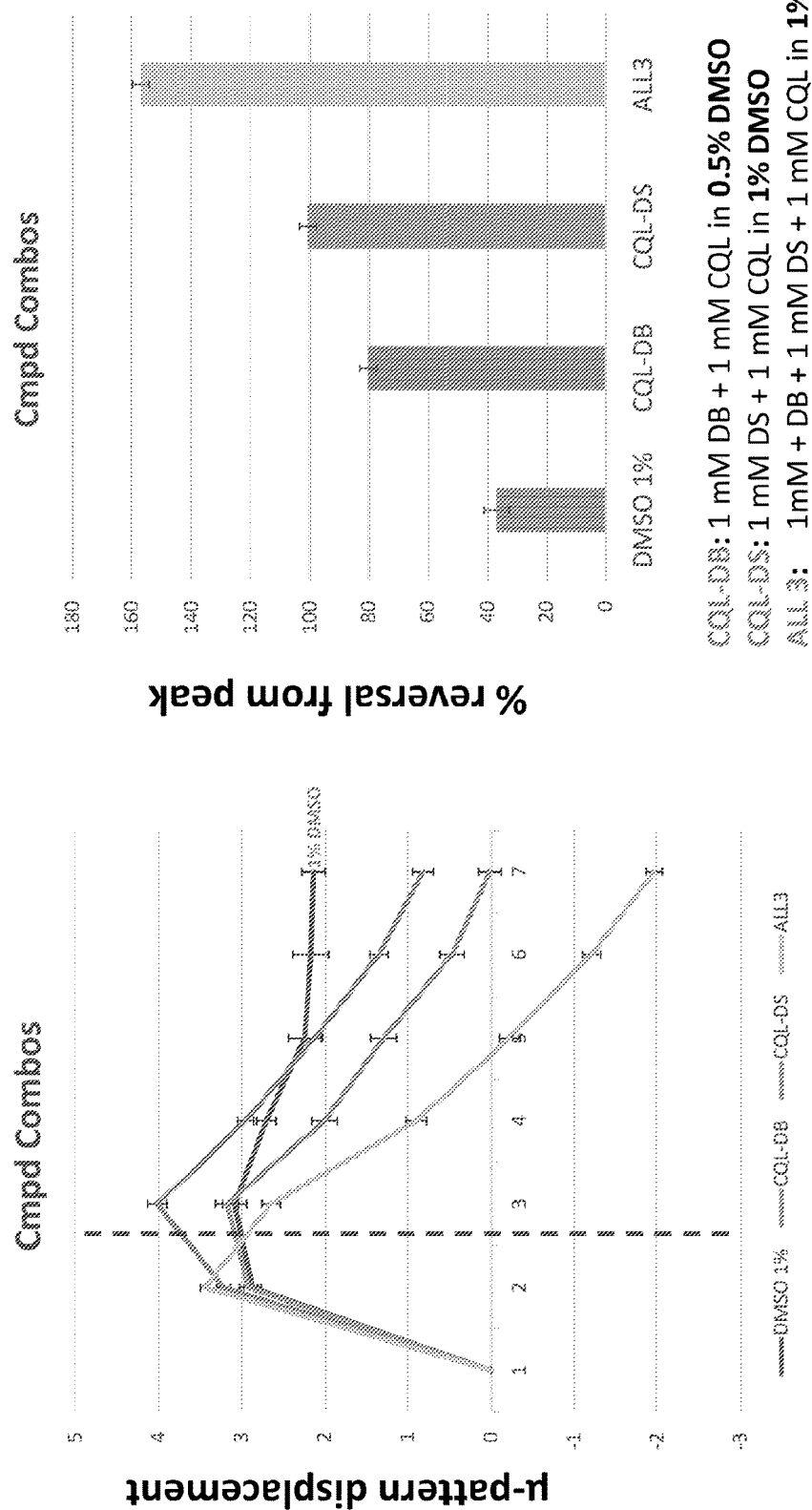
FIG. 2 shows results of various combinations of compounds tested.

FIG. 1 shows the results of individually tested compounds as a percentage reversal from peak contraction of the PVSMCs. FIG. 2 shows results of various combinations of compounds tested. FIG. 3 shows results with DB alone and in combination with SIN and FIG. 4 shows results with DS alone and in combination with SIN. FIG. 5 shows results with 3-CQL alone and in combination with SIN. The data in FIGS. 1-5 show that at low doses (10 µM), SIN was not effective by itself, but at 100 µM, it is extremely effective. However, there was synergy at low SIN doses with all of DB, DS and 3-CQL. And DB was also not potent alone but was in combination with 3-CQL or SIN.

In a second experiment, primary pulmonary SMCs were induced to contract using 10 µM phenylephernine (PE). PE was added after a baseline reading. The test compounds were added after a second timepoint and 800-1300 cells were assayed per trace, starting with FIG. 6. FIG. 6 shows individually tested compounds. FIG. 7 shows combinations of compounds. FIG. 8 shows DB alone and in combination with SIN. FIG. 9 shows DS alone and in combination with SIN. FIG. 10 shows 3-CQL alone and in combination with SIN. With the exception of an aberrant result with 3-CQL, the data with PE also show that at low doses (10 µM), SIN was not effective by itself, but at 100 µM it is extremely effective. However, there was synergy at low SIN doses with DB and DS, and possibly 3-CQL.

TABLE 1
Bitter agents
| Active name | Chemical structure |
|---|---|
| Denatonium Benzoate (DB) | 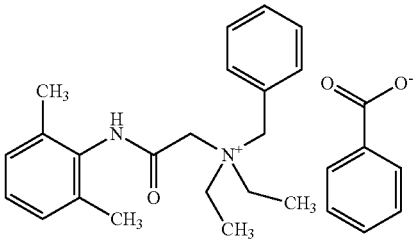 [SMILES: CC[N+](CC)(CC(=O)Nc1c(C)cccc1C)Cc1ccccc1 ; O=C([O-])c1ccccc1] |
| Denatonium Saccharide (DS) | 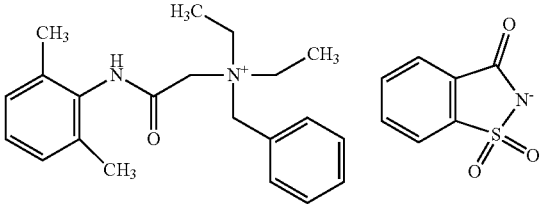 [SMILES: CC[N+](CC)(CC(=O)Nc1c(C)cccc1C)Cc1ccccc1 ; O=C1[N-]S(=O)(=O)c2ccccc21] |
| quinine | 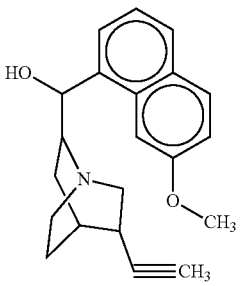 |
| Amarogentin | 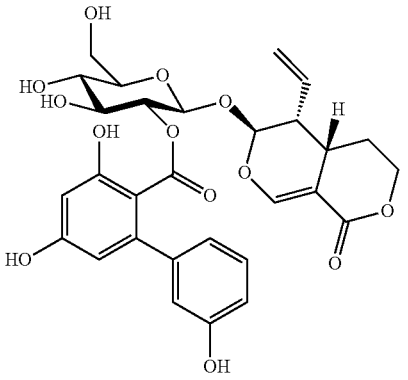<br>Amanogentin |
| Diphenidol | 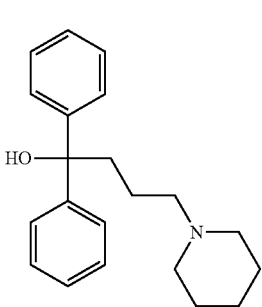 [SMILES: OC(CCCN1CCCCC1)(c1ccccc1)c1ccccc1] |

TABLE 1-continued

Bitter agents

| Active name | Chemical structure |
| --- | --- |
| Parthenolide | 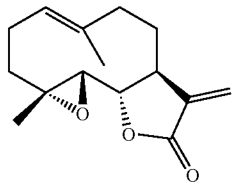 [SMILES: C=C1C(=O)O[C@H]2[C@H]1CC/C(C)=C/CC[C@@]1(C)O[C@@H]21] |
| Cromolyn | 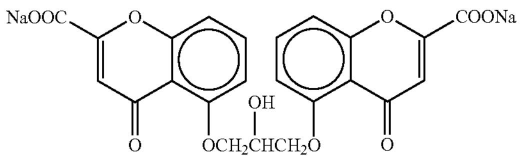 |
| Apomorphine | 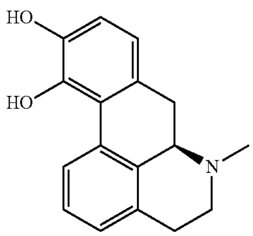 [SMILES: CN1CCc2cccc3c2[C@H]1Cc1ccc(O)c(O)c1-3] |
| Divinyl sulfoxide | 3) Divinyl sulfoxide |
| picrotoxinin | 4) Picrotoxinin |
| aristolochic acid | 1) Aristolochic Acid |

TABLE 1-continued

Bitter agents

| Active name | Chemical structure |
|---|---|
| falcarindiol | 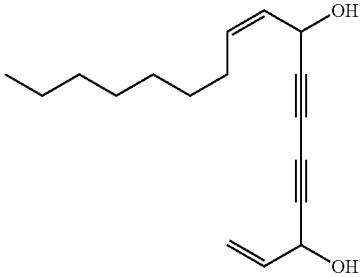 |

2) Falcarindiol

Denatonium, usually available as denatonium benzoate (under trade names such as BITTERANT-b, BITTER+ PLUS, Bitrex or Aversion) and as denatonium saccharide (BITTERANT-s), is believed to be the most bitter chemical compound known, with bitterness thresholds of 0.05 ppm for the benzoate and 0.01 ppm for the saccharide. It is used as an aversive agent (bitterants) to prevent inappropriate ingestion. Denatonium is used in denatured alcohol, antifreeze, nail biting preventions, respirator mask fit-testing, animal repellents, liquid soaps, and shampoos. It is not known to pose any long-term health risks.

An ideal bitter compound therapeutic should be safe to consume in the quantities required to elicit the desired physiologic response, and also activate a broad range of TAS2R receptor subtypes. Denatonium benzoate (DB) is a bitter substance and activates 8 TAS2R subtypes. It is also generally regarded as safe and is commercially added to toxic household products to discourage inadvertent consumption by children.

Quinine. Molecular Formula: $C_{20}H_{24}N_2O_2$ Molar Mass: 324.42 g·mol$^{-1}$
  ChemSpider ID: 84989
  Quinine is a medication used to treat malaria, babesiosis, and restless leg syndrome, taken orally or intravenously, although it is often also administered intramuscularly and rectally. It is also added to tonic water to confer bitter taste.

Amarogentin
  IUPAC name: [(2S,3R,4S,5S,6R)-2-[[(3S,4R,4aS)-4-Ethenyl-8-oxo-4,4a,5,6-tetrahydro-3H-pyrano[3,4-c]pyran-3-yl]oxy]-4,5-dihydroxy-6-(hydroxymethyl)oxan-3-yl]2,4-dihydroxy-6-(3-hydroxyphenyl)benzoate
  Chemical Formula: $C_{29}H_{30}O_{13}$
  Molar Mass: 586.55 g·mol$^{-1}$
  ChemSpider ID: 103033
  One of the most bitter compounds known, it is found in gentian root (*Gentiana lutea*) and also one of the most bitter substances.

Diphenidol
  Chemical Formula: $C_{21}H_{27}NO$
  Molar Mass: 309.44518
  ChemSpider ID: 2947
  Diphenidol is a muscarinic antagonist employed as an antiemetic and as an antivertigo agent. It is not marketed in the United States or Canada. The mechanism of action of Diphenidol on the vestibular system has not yet been elucidated.

Parthenolide
  IUPAC name (3aS,9aR,10aS,10bS,E)-6,9a-dimethyl-3-methylene-3a,4,5,8,9,9a,10a,10b-octahydrooxireno[2',3': 9,10]cyclodeca[1,2-b]furan-2(3H)-one
  Chemical Structure: $C_{15}H_{20}O_3$
  Molar Mass: 248.32 g·mol$^{-1}$
  Parthenolide is a sesquiterpene lactone of the germacranolide class which occurs naturally in the plant feverfew (*Tanacetum parthenium*), after which it is named.

Cromolyn
  Molar Mass 468.367
  ChemSpider: 2779
  Cromolyn (also referred to as cromolyn (USAN), cromoglycate (former BAN), or cromoglicate) is a mast cell stabilizer and can be given via several routes: topical: oral, nasal spray, inhaled, and eye drops.

Apomorphine
  Chemical Name: 5,6,6a,7-Tetrahydro-6-methyl-4H-dibenzo[de,g]quinoline-10,11-diol hydrochloride
  Molecular Formula: $C_{17}H_{17}NO_2 \cdot HCl \cdot \frac{1}{2}H_2O$
  CAS Number: 41372-20-7
  Apomorphine (brand names Apokyn, Ixense, Spontane, Uprima) is a morphine decomposition product that does not contain morphine or its skeleton and does not bind to opioid receptors. It does have activity as a non-selective dopamine agonist which activates both $D_2$-like and, to an order of magnitude lesser extent, $D_1$-like receptors. It also acts as an antagonist of 5-HT$_2$ and α-adrenergic receptors with high affinity. It is clinically used for Parkinson's Disease, Alzheimer's Disease, erectile dysfunction, as well as for alcohol and morphine addiction.

Picrotoxinin
  picrotoxinin ($C_{15}H_{16}O_6$; CAS #17617-45-7).
  Picrotoxinin is derived naturally in the fruit of the *Anamirta cocculus*. Due to its interactions with the inhibitory neurotransmitter GABA, picrotoxin acts as a stimulant and convulsant.

Falcarindiol
  IUPAC name: (3R,8S,9Z)-1,9-Heptadecadiene-4,6-diyne-3,8-diol.
  ChemSpider: 4444558
  Chemical Formula: $C_{17}H_{24}O_2$
  Molar mass: 260.371
  Falcarindiol is a polyacetylene found in carrot roots which has antifungal activity. Falcarindiol is the main compound responsible for bitterness in carrots.

A treatment that could utilize a compound with low inherent toxicity to trigger extra-oral bitter receptors in the gut, brain, and other regions such as adipocytes provides a relatively safe means to decrease appetite and increase satiety selectively without the "off-target" CNS effects or GI disturbance typical of other obesity medications.

An ideal bitter compound therapeutic should be safe to consume in the quantities required to elicit the desired physiologic response, and also activate a broad range of TAS2R receptor subtypes. Denatonium benzoate (DB) is a bitter substance and activates 8 TAS2R subtypes. It is also generally regarded as safe and is commercially added to toxic household products to discourage inadvertent consumption by children. Quinine is also an ingested alkaloid that is safe in small quantities and found in soda water and used as an anti-malarial medication. It activates 9 TAS2R subtypes.

Coating a bitter compound, such as DB or quinine, in a tasteless ingestible capsule allows a pharmaceutical composition to bypass induction of aversive responses mediated by oral TAS2R receptors. But it still provides anorexigenic effects via stimulation of gut receptors, brain and adipocyte TAS2R receptors, after absorption into the circulation.

In another embodiment, the bitter agent is apomorphine, which is a breakdown product of morphine. It is used currently as a drug for Parkinson's but delivered subcutaneously. Apomorphine oral availability is approximately only 4%. It has current veterinary use as an agent to induce vomiting in dogs. Aside from also being a bitter alkaloid, it also is a dopamine agonist (D2 receptor).

Example 1

This example illustrates a synthesis of various bitter agents provided herein.

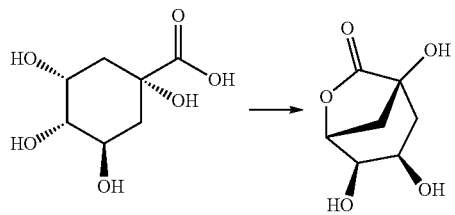 [SMILES: O=C(O)[C@]1(O)C[C@@H](O)[C@@H](O)[C@H](O)C1 ; O=C1O[C@@H]2C[C@@]1(O)C[C@@H](O)[C@H]2O]

1,5-quinide. Quinic acid (25 g, 130.1 mmol) and p-toluenesulfonic acid (500 mg, 2.622 mmol) were dissolved in anhydrous toluene (350 mL) and dimethylformamide (50 mL) in an oven-dried round bottom flask. The flask was equipped with a Dean-Stark apparatus and the vessel was refluxed overnight while stirring. The mixture was cooled to room temperature and toluene was evaporated. The remaining solution was cooled in an ice bath and solid was precipitated by the addition of a hexanes and ethyl acetate mixture (4:1). The precipitate was filtered and rinsed with diethyl ether to give a white solid (6.078 g, 26.8% yield). $^1$H NMR (600 MHz, Methanol-$d_4$) δ 4.70 (dd, J=6.0, 4.9 Hz, 1H), 3.98 (t, J=4.6 Hz, 1H), 3.70 (ddd, J=11.2, 6.6, 4.4 Hz, 1H), 2.47 (d, J=11.4 Hz, 1H), 2.22 (ddd, J=11.4, 6.0, 3.0 Hz, 1H), 2.03 (dddd, J=11.8, 6.6, 2.9, 0.8 Hz, 1H), 1.87 (t, J=11.6 Hz, 1H).

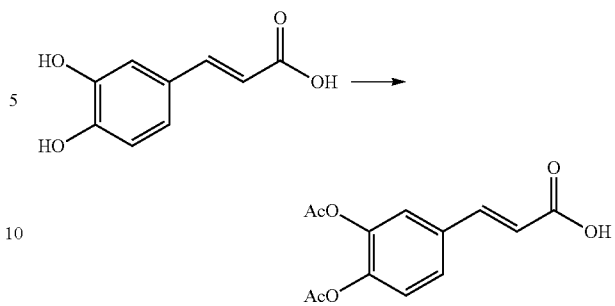

3,4-Diacetoxycinnamic acid. A mixture of caffeic acid (25 g, 138.8 mmol) and pyridine (11.18 mL, 138.8 mmol) was added acetic anhydride (65.59 mL, 603.8 mmol) and stirred at room temperature overnight. The solvent was evaporated and the solid was rinse with water followed by diethyl ether and dried to obtain a white solid (19.56 g, 53.3%). $^1$H NMR (600 MHz, DMSO-$d_6$) δ 12.48 (broad s, 1H), 7.66 (d, J=2.1 Hz, 1H), 7.63 (dd, J=8.4, 2.1 Hz, 1H), 7.56 (d, J=16.0 Hz, 1H), 7.31 (d, J=8.3 Hz, 1H), 6.53 (d, J=16.0 Hz, 1H), 2.29 (d, J=4.4 Hz, 6H).

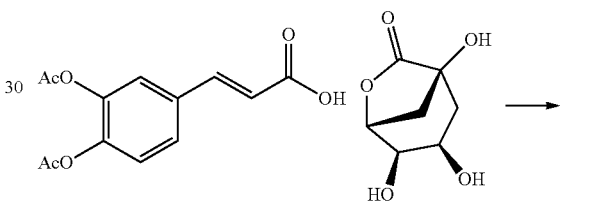

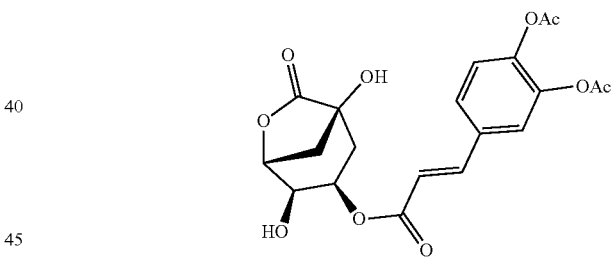

3,4-Diacetoxycinnamoylquinic acid lactone. To 3,4-diacetoxycinnamic acid (4 g, 15.14 mmol) suspended in anhydrous dichloromethane (70 mL) under argon was added oxalyl chloride (1.3 mL, 15.14 mmol) followed by anhydrous DMF (0.6 mL). The reaction stirred for two hours and the solution became transparent. 1,5-quinide and 4-Dimethylaminopyridine dissolved in a pyridine dichloromethane mixture (1:2.5, 140 mL) was added to the reaction vessel. The mixture was warmed to 35° C. and stirred for 4 hours. The solvent was evaporated and the solid was purified by flash chromatography (DCM/MeOH 4%) to yield a white solid (3.605 g, 56.7%). $^1$H NMR (600 MHz, Chloroform-d) δ 7.66 (d, J=15.9 Hz, 1H), 7.40 (ddd, J=8.4, 2.1, 0.5 Hz, 1H), 7.37 (d, J=2.1 Hz, 1H), 7.23 (d, J=8.3 Hz, 1H), 6.39 (d, J=16.0 Hz, 1H), 5.06 (ddd, J=11.3, 6.9, 4.3 Hz, 1H), 4.84 (dd, J=6.0, 4.9 Hz, 1H), 4.38 (board s, J=2.7 Hz, 1H), 2.71 (d, J=11.8 Hz, 1H), 2.57 (d, J=2.9 Hz, 1H), 2.36 (ddd, J=11.8, 6.0, 2.8 Hz, 1H), 2.30 (d, J=2.3 Hz, 6H), 2.26 (ddd, J=12.7, 6.9, 2.9, 0.8 Hz, 1H).

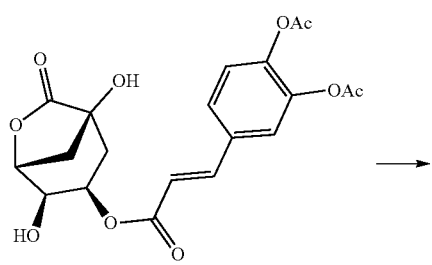

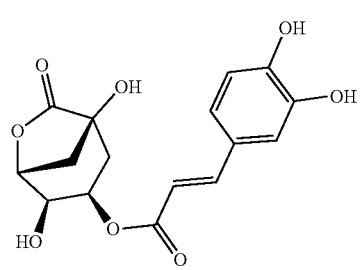

3-Caffeoyl-1,5-quinide. To a solution of 3,4-Diacetoxycin-namoylquinic acid lactone (3 g, 7.137 mmol) in Ethanol (60 mL) was added ammonium hydroxide (1.5 mL, 14.8 M) and was stirred for 1 hour. Acidified with hydrochloric acid (IM) and extracted with ethyl acetate. The organic extractions were dried over sodium sulfate, filtered and the solvent was evaporated. The solid was recrystallized from hot ethyl acetate to obtain a white solid (1.725 g, 71.9%). $^1$H NMR (600 MHz, Methanol-$d_4$) δ 7.62 (d, J=15.9 Hz, 1H), 7.05 (d, J=2.1 Hz, 1H), 6.96 (dd, J=8.3, 2.1 Hz, 1H), 6.78 (d, J=8.2 Hz, 1H), 6.30 (d, J=15.9 Hz, 1H), 4.91 (ddd, J=11.4, 6.8, 4.3 Hz, 1H), 4.74 (dd, J=6.0, 5.0 Hz, 1H), 4.29 (t, J=4.6 Hz, 1H), 2.56 (d, J=11.6 Hz, 1H), 2.30 (ddd, J=11.5, 6.0, 2.8 Hz, 1H), 2.19-2.13 (m, 1H), 2.08 (t, J=11.7 Hz, 1H).

Example 2

Synthesis of Denatonium Acetate

Step 1: Synthesis of Denatonium Hydroxide from Lidocaine

To a reflux apparatus add 25 g of lidocaine, 60 ml of water and 17.5 g of benzyl chloride with stirring and heating in 70-90° C. The solution needs to be heated and stirred in the before given value for 24 h, the solution needs to be cooled down to 30° C. The unreacted reagents are removed with 3×10 mL of toluene. With stirring dissolve 65 g of sodium hydroxide into 65 mL of cold water and add it to the aqueous solution with stirring over the course of 3 h. Filter the mixture, wash with some water and dry in open air. Recrystallize in hot chloroform or hot ethanol.

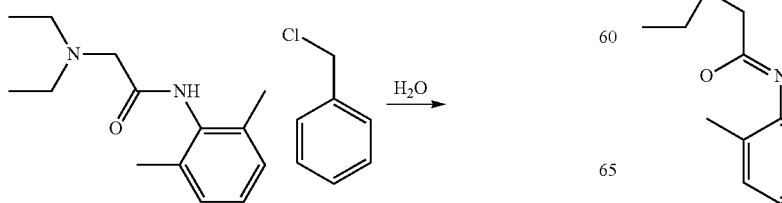

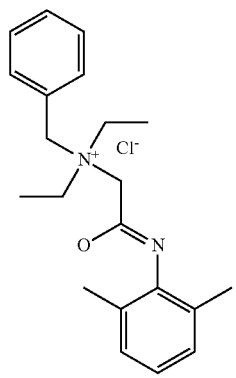

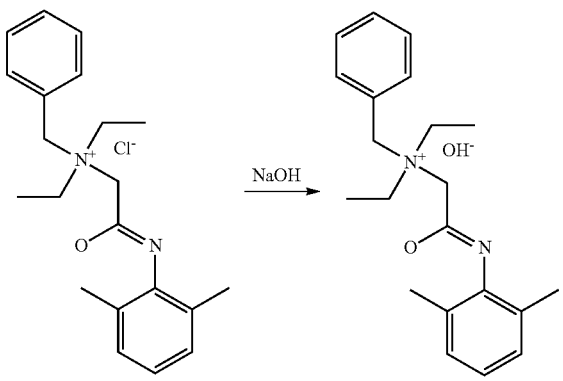

Step 2: Preparation of Denatonium Acetate from Denatonium Hydroxide.

To a reflux apparatus 10 g of denatonium hydroxide (MW: 342.475 g/mol, 0.029 mol), 20 mL of acetone, and 2 g of acetic acid glacial (0.033 mol) dissolved in 15 mL of acetone is added, the mixture is stirred and heated to 35° C. for 3 h. Then evaporated to dryness and recrystallized in hot acetone.

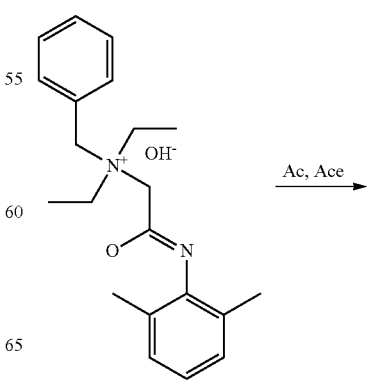

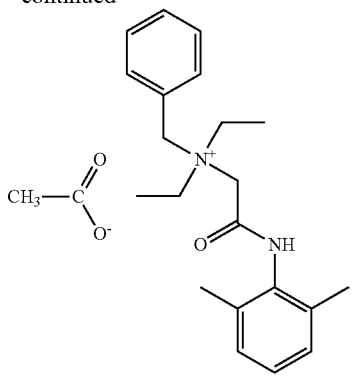

We claim:

1. A method for treating pulmonary arterial hypertension (PAH) with an orally administered therapeutic formulation comprising a bitter agent selected from the group consisting of denatonium acetate (DA), denatonium citrate (DC), denatonium maleate (DM), and 3-caffeoylquinic-1,5-lactone (3-CQL).

2. The method for treating PAH with an orally administered therapeutic formulation of claim 1, further comprising a PDE-5 inhibitor.

3. The method for treating PAH with an orally administered therapeutic formulation of claim 2, wherein the PDE-5 inhibitor is selected from the group consisting of sildenafil, tadalafil, vardenafil, zaprinast, udenafil, microdenafil, lodenafil, and avanafil.

4. The method for treating PAH with an orally administered therapeutic formulation of claim 3, wherein the PDE-5 inhibitor is sildenafil as an oral daily dose of from about 10 mg to about 100 mg administered once or twice daily.

5. The method for treating PAH with an orally administered therapeutic formulation of claim 1, wherein the bitter agent is DA.

6. The method for treating PAH with an orally administered therapeutic formulation of claim 5, wherein the daily dosage of DA for an adult is from about 10 mg to about 400 mg.

7. The method for treating PAH with an orally administered therapeutic formulation of claim 6, wherein the daily dosage of DA for an adult is from about 10 mg to about 200 mg.

8. The method for treating PAH with an orally administered therapeutic formulation of claim 1, wherein the daily dosage of DA for an adult is from about 10 mg to about 100 mg.

9. The method for treating PAH with an orally administered therapeutic formulation of claim 8, wherein the daily dosage of 3-CQL or CGA for an adult is from about 10 mg to about 5000 mg.

* * * * *

UNITED STATES PATENT AND TRADEMARK OFFICE
CERTIFICATE OF CORRECTION

Page 1 of 1

PATENT NO. : 12,268,660 B2
APPLICATION NO. : 17/257458
DATED : April 8, 2025
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 847 days.

Signed and Sealed this
Sixth Day of January, 2026

John A. Squires
*Director of the United States Patent and Trademark Office*